United States Patent Office

Plant Pat. 1,647
Patented Oct. 8, 1957

1,647

HARDY PEACH TREE

William W. Moore, Sandy Spring, Md.

No Drawing. Application August 3, 1953, Serial No. 372,210

1 Claim. (Cl. 47—62)

This invention relates to a new and distinct variety of peach tree and more particularly to a mutation of the non-patented variety Elberta peach.

I started propagation of this variety of peach tree in 1928 with ten scions from an unnamed and unpatented seedling peach tree then about ten years old, which had borne seven large annual crops of consistently good fruit, for the purpose of developing a commercial orchard variety at my orchard, Sandy Spring, Maryland. The seedling peach tree was not found nor grown by me and as I recognized the new and distinct characteristics of the fruit of this tree, the owner of the tree gave me grafts from this tree for the express purpose of developing this new strain knowing that I had the necessary knowledge and experience for this purpose.

From the original scions ten trees were grafted on selected native root stock, and these trees grew vigorously and bore annual crops after the third year of large late peaches. No trees were sold or given away.

The following description of the 1953 crop is given as characteristic of the tree and its fruit:

Tree:

*Size.*—Very large; very vigorous; upright-spreading; dense; wide vase form; of rapid growth and early maturity.

*Trunk.*—Medium to large.

*Branches.*—Moderate to large; stocky, willowy, strong; not brittle; crotches well made. Carries heavy loads of fruit by bending, not breaking as expected.

*Bark.*—Bright; light gray.

*Lenticels.*—Large, numerous, yet not closely crowded.

*Productivity.*—Very productive; regular bearer in spite of unfavorable weather conditions.

Leaves:

*Size.*—6 to 7 inches long; 1½ to 1¾ inches wide.

*Shape.*—Very regularly glandular; crenate-serrate; margin undulate; closely so at base (crinkled at base); somewhat corduplicate (folded along rib).

*Tip.*—Long; acuminate; distinctly falcate (sythe-shaped).

*Thickness.*—Subcoriaceous (leathery).

*Color.*—Deep green.

*Petioles.*—Medium length.

*Glands.*—Medium; 2 to 6; mostly opposite.

Fruit: Harvested September 4, 1953, 160 days after blossoming. Hale, Shippers, Elberta and Brackett, all unpatented varieties of locally grown peaches, harvested over a week previous. Rio Oso Gem (Plant Patent No. 84) harvested a few days before. The present variety was soft ripe but hung onto the trees almost as tightly as at firm ripe stage.

*Size.*—Uniform; large, a few medium. Even on heavily-laden limbs, where fruits hung cheek to cheek, the size was uniformly large. Average axial diameter 2¾ to 2⅞ inches, some 3 inches. Average transverse in suture plane, 3 to 3¼ inches, giving general appearance of slightly oblong fruit.

*Flesh.*—Medium grain, deep yellow, juicy, resistant to dry rot.

*Form.*—Uniform; slightly oblong; some compression toward suture.

*Suture.*—Fairly prominent; very slight cracking; depressed about ½ inch beyond pistil point.

*Ventral surface.*—Flat to slight rounding, unequally lipped toward apex.

*Cavity.*—Narrow, acute; moderately deep; some elongation in suture plane; suture showing on one side.

*Base.*—Rounded; truncate; very slightly oblique.

*Apex.*—Prominently rounded, having almost a point; pistil point apical.

*Skin.*—Thin; no cracking.

*Down.*—Very light; very short.

*Color.*—Rich, light yellow; clear bright ground color; deep purplish red where exposed with lighter splashes and mottlings. Red color not solid, but stippled, screened and splashed. Practically all surface has some red pigment.

Stone or pit: Free when ripe.

*Size.*—Medium; 1½ to 1¾ inches long; 1⅛ inches wide; ⅝ inch thick.

*Shape.*—Flattened; obovoid; distinctly wing-edged; widest above the middle. Hilum—oval; apex—acuminate; sides unequal. Surface—unequally furrowed; pits few, irregular; ridges broad; smoothly rounded. Color—light to medium brown. No tendency to split.

I have now had the grafted or budded trees in bearing for enough seasons to establish the characteristics of the fruit, and have asexually reproduced and successfully propagated at Sandy Spring, Maryland, a considerable number of young trees from grafts and buds taken from the trees resulting from the original grafts, all having the same characteristics of hardiness and late ripening choice fruit.

These trees have never failed to produce a crop notwithstanding cold winters when the temperature reached zero degrees Fahrenheit and some other varieties of peach tree in the vicinity, such as Hale, Shippers, Brackett and Alberta, all unpatented varieties, and Rio Oso Gem (Plant Patent No. 84), were frozen or the crop winter killed, and notwithstanding spring frosts damaging these varieties of peaches growing nearby.

The tree is self-pollinated and the flower resembles that of the Elberta peach but is slightly deeper pink in color, and is more resistant to frost and winter-kill. The fruit ripens about ten days later than the Elberta peach, usually during the first two weeks in September.

I have shipped peaches of this variety as far as Boston, Massachusetts, where they arrived in good condition. The fruit has been found to be excellent for eating, preserving, canning and freezing.

I claim:

A new and distinct variety of peach tree as described, characterized as to novelty to the Elberta peach tree variety (not patented) by its hardiness and resistance to cold and the late time of ripening of the fruit.

No references cited.